United States Patent [19]

Kawata et al.

[11] Patent Number: 4,565,526
[45] Date of Patent: Jan. 21, 1986

[54] ORTHODONTIC APPLIANCE

[75] Inventors: Terushige Kawata, Tokushima; Takashi Kobayashi, Mino; Katsuyuki Nakagawa, Osaka, all of Japan

[73] Assignee: Sankin Industry Co., Ltd., Osaka, Japan

[21] Appl. No.: 660,365

[22] Filed: Oct. 12, 1984

[30] Foreign Application Priority Data

Jun. 28, 1984 [JP] Japan ................................ 59-131962

[51] Int. Cl.$^4$ .............................................. A61C 7/00
[52] U.S. Cl. ......................................... 433/8; 433/14; 433/18
[58] Field of Search ...................... 433/18, 8, 9, 16, 14

[56] References Cited

U.S. PATENT DOCUMENTS

| | | | |
|---|---|---|---|
| 1,323,141 | 11/1919 | Young | 423/14 |
| 3,353,271 | 11/1977 | Blechman | 32/14 |
| 3,793,730 | 2/1974 | Begg et al. | 433/16 |
| 3,881,252 | 5/1975 | Andrews | 433/16 |
| 3,984,915 | 10/1976 | Noble et al. | 32/14 |
| 4,068,379 | 1/1978 | Miller et al. | 433/9 |
| 4,424,030 | 1/1984 | Smiley et al. | 433/18 |

Primary Examiner—Robert Peshock
Attorney, Agent, or Firm—Pahl, Lorusso & Loud

[57] ABSTRACT

An orthodontic appliance for correcting teeth in a patient's mouth, has a bracket having a slot or groove and adapted to be secured to a tooth of the patient by means of an adhesive, a correcting wire placed in the slot or groove of the bracket, a magnet body having at least one magnet element, and a holder detachably attached to the bracket for holding the magnet body.

24 Claims, 41 Drawing Figures

ORTHODONTIC APPLIANCE

BACKGROUND OF THE INVENTION

This invention relates to a magnetic orthodontic appliance through which corrective traction is applied to teeth of a patient by magnetically generated force derived from permanent magnets in order to correct the positions of the teeth.

Conventional orthodontic appliances using magnetic traction for producing corrective displacement of the patient's teeth have the following defects:

(1) The corrective traction force is not enough to produce corrective displacement of the patient's teeth in practice. It is not convenient to use a magnet having a thickness as great as 3.2-3.5 mm is in the mouth.

(2) It is difficult to adjust the magnetic force or corrective force while viewing the teeth to be corrected.

(3) Corrective movement of the teeth is limited to one direction (a mesiodistal direction). Accordingly, three-dimensional movement of the teeth is almost impossible.

(4) Before a magnet is fixedly mounted on a tooth, the magnet easily moves toward the adjacent magnet through magnetic traction. For that reason, an orthodontist must press the magnet against the tooth until the bonding agent hardens so that the magnet is completely fixed thereto.

(5) When the patient bites, a magnet is often broken due to its large size.

(6) It is difficult to remove the magnets for adjustment of the corrective force.

(7) A correcting or ligature wire must be tightened or strengthened by repeated adjustments by a dentist for the purpose of adjustment to the proper corrective force.

OBJECTS OF THE INVENTION

It is an object of this invention to provide an orthodontic appliance wherein a magnet or magnets can be easily attached and removed so as to adjust the corrective force exerted on misaligned teeth of a patient.

It is another object of this invention to provide an orthodontic appliance through which an ideal corrective force is exerted on misaligned teeth of a patient to correct precisely the relative positions of the teeth thereby to create a proper bite of the teeth, proper spacing and proper curvature of the mouth.

It is yet another object of this invention to provide an orthodontic appliance wherein the traction force exerted on teeth of a patient can be adjusted by replacement of magnets after a specific orthodontic design is employed, so that repeated removals of the whole orthodontic appliance can be avoided.

DETAILED DESCRIPTION OF THE PREFERRED EMBODIMENTS

FIGS. 1 to 13 show an orthodontic appliance according to a first embodiment of this invention. The orthodontic appliance includes a magnet attachment 1 and a bracket 2 with a mesh base.

Figure 14:
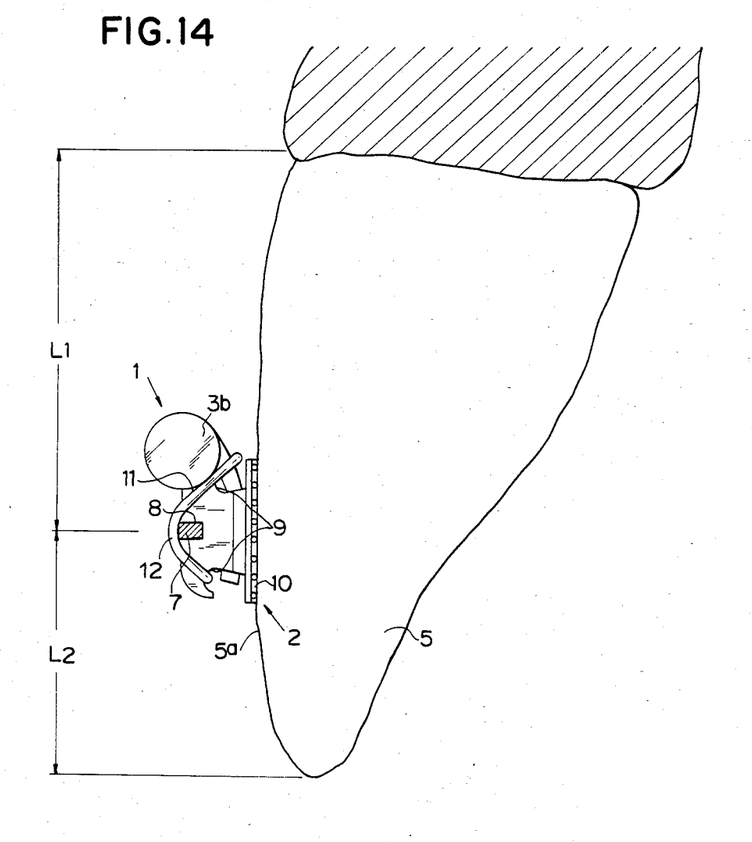
FIG. 14 is a side view showing a condition in which the orthodontic appliance of FIG. 1 is attached to teeth of a patient.
Figure 15:
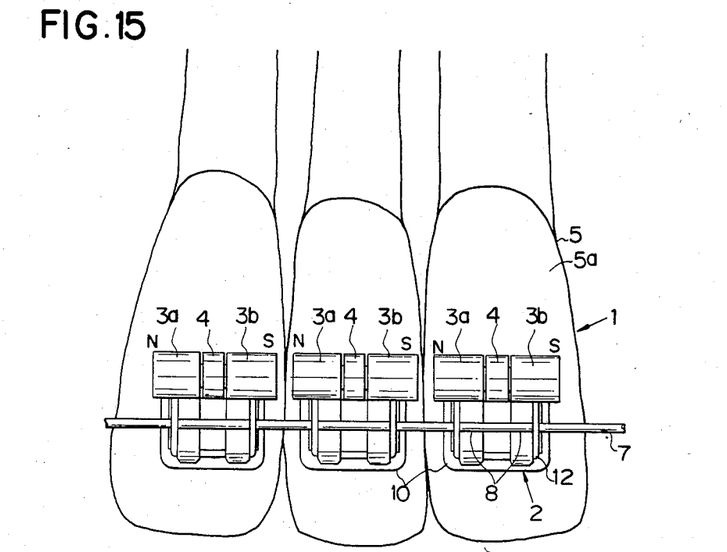
FIG. 15 is a front view showing a condition in which teeth of a patient are completely corrected to their proper positions.

As shown in FIG. 14, the bracket 2 is attached on a surface 5a of a tooth 5 by means of an adhesive.

Figure 1:
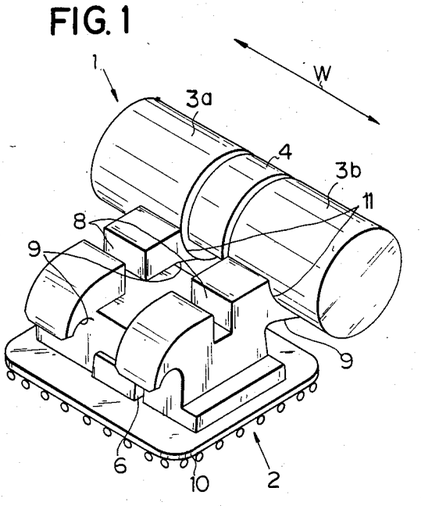
FIG. 1 is a perspective view showing an orthodontic appliance according to a first embodiment of this invention.
Figure 2:
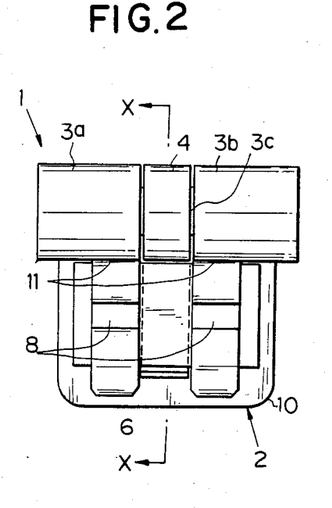
FIG. 2 is a front view of the orthodontic appliance shown in FIG. 1.
Figure 3:
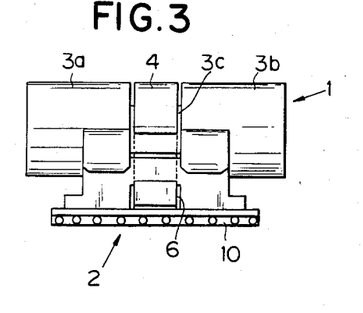
FIG. 3 is a plan view of the orthodontic appliance shown in FIG. 1.
Figure 4:
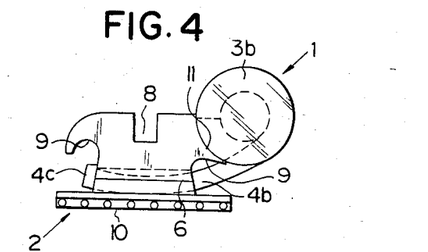
FIG. 4 is a right side view of the orthodontic appliance shown in FIG. 1.
Figure 5:
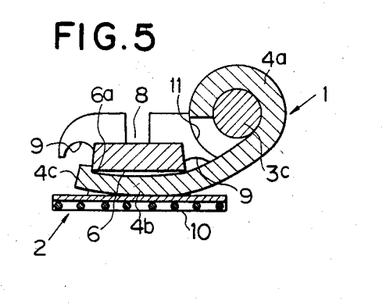
FIG. 5 is a sectional view taken along the line X—X of FIG. 2.
Figure 6:
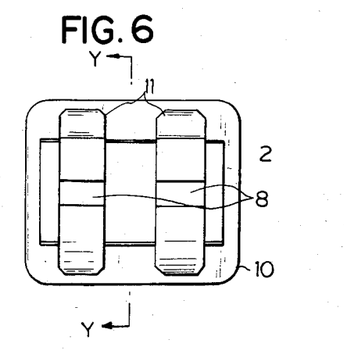
FIG. 6 is a plan view showing a bracket used in the orthodontic appliance shown in FIG. 1.
Figure 7:
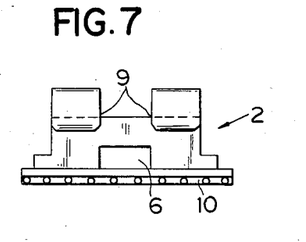
FIG. 7 is a front view of the bracket shown in FIG. 6.
Figure 8:
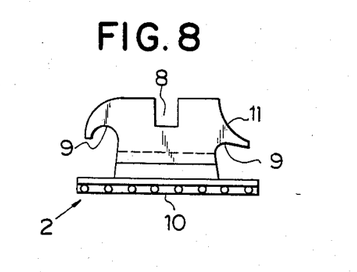
FIG. 8 is a side view of the bracket shown in FIG. 6.
Figure 9:
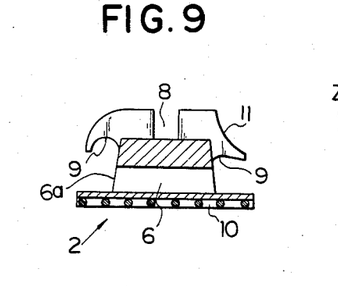
FIG. 9 is a sectional view taken along the line Y—Y of FIG. 6.
Figure 10:
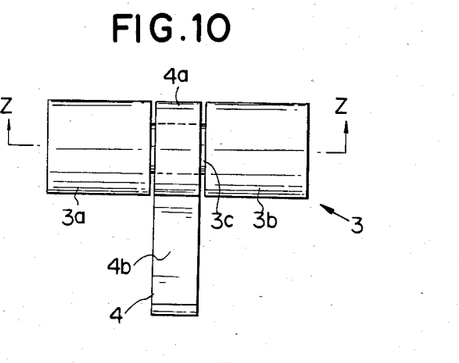
FIG. 10 is a rear plan view showing a magnet attachment used in the orthodontic appliance shown in FIG. 1.
Figure 11:
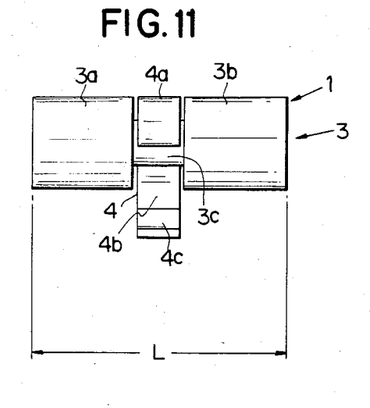
FIG. 11 is a front view of the magnet attachment shown in FIG. 10.
Figure 12:
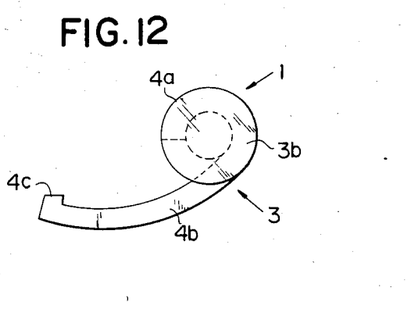
FIG. 12 is a side view of the magnet attachment shown in FIG. 10.

The magnet attachment 1 has a magnet body 3 having a magnetic traction in a direction shown by the arrow W in FIG. 1 and a holder 4 such as a pin type holder. The holder 4 holds the magnet body 3 at one end and is detachably attached at its other end portion to a securing opening 6 in the bracket 2 as best shown in FIG. 5.

Figure 13:
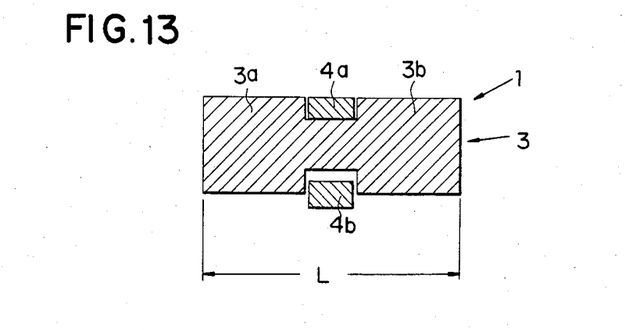
FIG. 13 is a sectional view taken along the line Z—Z in FIG. 10.

In the first embodiment, the magnet body 3 has a pair of cylindrical magnet elements 3a, 3b and a joint portion 3c placed therebetween. The holder 4 holds the joint portion 3c. The magnet elements 3a, 3b have a common axis and opposite poles so as to produce a magnetic traction in the direction of the arrow W. The magnet elements 3a, 3b may vary in size and strength, but preferably together have a full length L of 2.0–20.0 mm (FIG. 13). Various types of magnetic materials may be utilized, but for the best results rare earth magnets are preferable such as Sm-Co magnets, CORMAX magnets (tradename of Sumitomo Special Metals Co., Ltd.) or NEOMAX magnets (tradename of Sumitomo Special Metals Co., Ltd.). Incidentally, CORMAX magnet is powder-metallurgically processed inter-metallic compound of cobalt and rare earth metal. NEOMAX magnets are sintered alloy magnets contain neodymium and iron-boron as main materials and having a tetragonal system. NEOMAX magnets have excellent characteristics as compared with the conventional cobalt and rare earth metal magnets. For instance, (BN)max and specific gravity thereof are 35 MGO and 7.4 gr/cm3, respectively.

Although the shape of the magnet elements 3a, 3b may vary, they are preferably of a cylindrical shape having a diameter of 1.0–3.0 mm.

It is preferable to treat the magnet elements by coating, ion-plating or galvanizing in view of the oral environment. The magnet elements may be pre-treated by impregnation so as to improve corrosion resistance.

The holder 4 is made of an elastic metal such as Ni-Cr, Co-Cr or SUS. As shown in FIGS. 4–5 and FIGS. 11–13, the holder 4 is preferably curved in an arch shape such a "9" shape for the purpose of ensuring and simplifying the elastic attachment thereof to the bracket 2. As shown in FIG. 5, the holder 4 has a portion 4a for holding the joint portion 3c of the magnet body 3 at its one end portion and a portion 4b at its other end portion to be inserted into the securing opening 6 of the bracket 2 so as to be secured thereto. A protruding stop 4c is formed at the end portion 4b of the holder 4 in order to prevent it from slipping out of position by engaging an edge 6a of the opening 6.

The bracket 2 may be an edgewise mesh bracket, edgewise bracket, semi-wedge bracket, torqued "T" slot bracket, or non-torqued "T" slot bracket.

In the embodiments shown in FIGS. 1–9 and FIGS. 14–15, the bracket 2 is provided with the above-described securing opening 6 for the holder 4, a slot or groove 8 in which a correcting wire 7 is placed, a mesh base 10 fixedly mounted on the surface 5a of the tooth 5, a magnet base 11 on which the magnet elements 3a, 3b are placed, and four wings 9 onto which a ligature or elastic wire 12 is secured so as to fix the correcting wire 7 in the slot or groove 8 of the bracket 2.

The wings 9 function as a hook means for the ligature or elastic wire 12.

Figure 17:
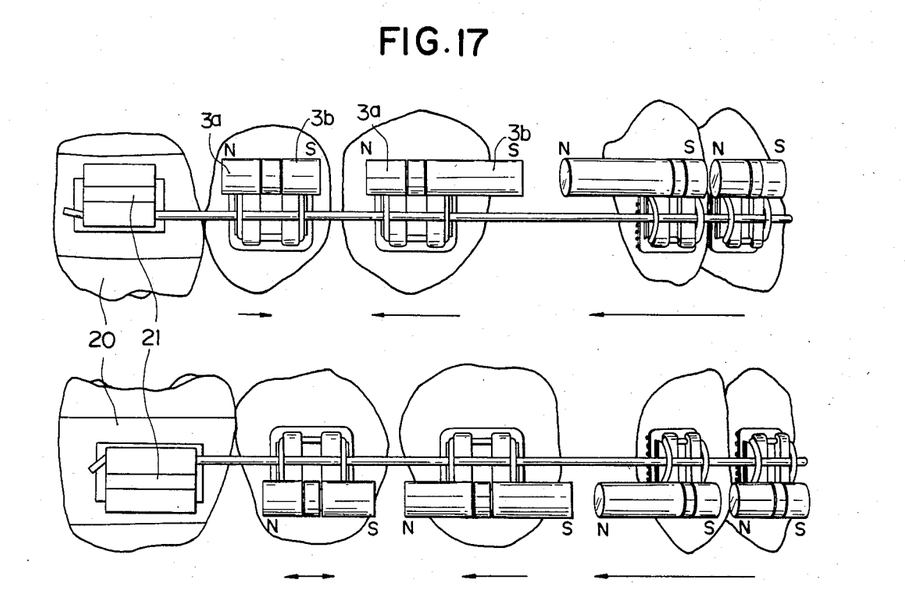
FIG. 17 shows movement of misaligned teeth toward molar teeth according to the first embodiment of this invention.

As shown in FIGS. 14 and 17, the bracket 2 is attached to the tooth 5 in such a manner that the mesh base 10 is fixed on the surface 5a of the tooth 5 by means of a dental adhesive. The correcting wire 7 is arranged in the slot or groove 8. The cross-sectional shape of the groove 8 may be rectangular or round, depending on the cross-sectional shape of the correcting wire 7.

The mesh base 10 may be made of mesh or net material only, or a combination of a thin metal plate and a mesh material, and has a configuration corresponding to a tooth to be corrected.

The magnet base 11 has a seat portion corresponding in shape to the magnet elements 3a, 3b so as to seat them thereon.

The dental adhesive may be made of a MMA resin, or Bis-GMA resin or well-known orthodontic resin such as SYSTEM I (trademark), UNITE (trademark), DYNA-BOND (trademark), "CONCISE" (trademark) and RIGHT ON (trademark).

Figure 16:
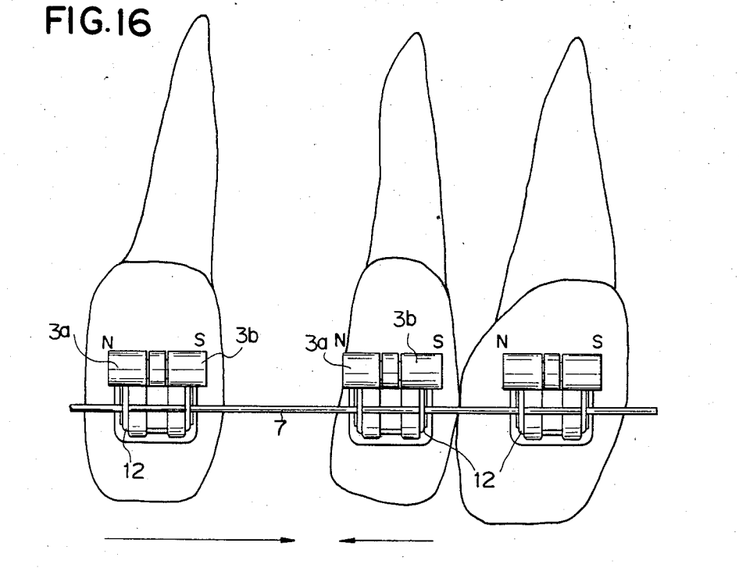
FIG. 16 shows movement of teeth to be corrected according to the first embodiment of this invention.

In operation, as shown in FIGS. 16 and 17, a plurality of brackets 2 are fixed on a plurality of predetermined upper and lower teeth by the dental adhesive. (Referring to FIG. 14, each bracket 2 is positioned in such a way that L1 and L2 are 1.5–6.0 mm and 3.0–4.5 mm, respectively.) Buccal tube means 21 are also fixed to upper and lower molars 20 by the dental adhesive. Thereafter, the correcting wires 7 are set on the buccal tube means 21 and the slots or grooves 8 of the brackets 2 fixed on the teeth 5. The ligature or elastic wires 12 are hooked onto the wings 9 so that the correcting wires 7 are securely fixed to the brackets 2.

In such a condition, a constant corrective force created by the correcting wires 7 is exerted on the teeth that need to be moved in a mesiodistal direction. As a result, the teeth are brought near an ideal arch line to some extent.

Next, after the elastic or ligature wires 12 are tentatively removed from the brackets 2, one end portion 4b of the holder 4 which holds the magnet body 3 at its other end portion 4a is inserted into the securing opening 6 of each brackets 2 so that the magnet elements 3a, 3b are placed on the seat portion of the magnet base 11. Then the elastic or ligature wires 12 are again set on the brackets 2 so as to fix the correcting wire 7 and the holder 4 to the bracket 2.

In this condition, opposite poles of the magnet elements 3a, 3b are located facing each other in such a manner that the teeth will move together so as to close the spaces between the adjacent teeth as shown by the arrows in FIGS. 16 and 17 due to the magnetic traction force. Also, the teeth move in a mesiodistal direction due to the elastic force of the correcting wires 7 placed in the grooves 8 of the brackets 2. In other words, the teeth 5 move in a three-dimensional direction, for instance, in respect to torque, angulation and height thereof.

The step of bending the correcting wire 7 can be omitted although it is preferably bent to a minor degree.

Various types of magnet attachments 1 can be exchanged in order to adjust corrective forces and particularly magnetic forces so as to correct perfectly and smoothly the misaligned teeth within a short time. For instance, a relatively long magnet element can be exchanged for successively shorter magnet elements in a step-by-step method for the purpose of gradually decreasing the traction force. Various magnet elements having different magnet forces and/or shapes can be selectively used. In such a case, the brackets 2 remain to be fixed to the teeth. Even if the same magnet elements 3a, 3b are used, the magnetic traction forces can be adjusted by changing the distances between the adjacent magnet elements. Also, by bending the holder 4 of the magnet attachment 1, the orientation of the magnetic force and a distance between it and a gum can be adjusted.

Preferably, the magnet elements 3a, 3b are positioned near the gum as shown in FIGS. 16 and 17 so that a patient can feel comfortable. It is also preferable that the height of the orthodontic appliance attached on teeth be about 2 mm in the case of the bracket 2 only and about 3 mm in the case of the combination of the bracket 2 and the magnet attachment 1.

Before the magnet attachments 1 are attached to the brackets 2, the brackets 2 are fixed on the teeth by the adhesive. After the adhesive hardens, the magnet attachments 1 are attached to the brackets 2. Thus, it is easy for a dentist to exactly position the brackets 2 on the teeth.

Figure 18:
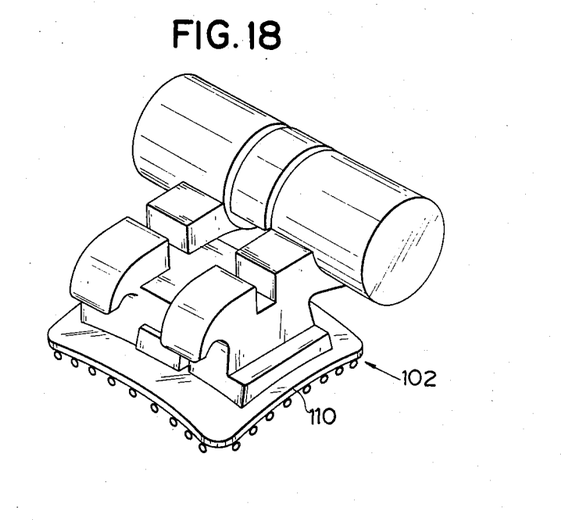
FIG. 18 is a perspective view showing an orthodontic appliance according to a second embodiment of this invention.
Figure 19:
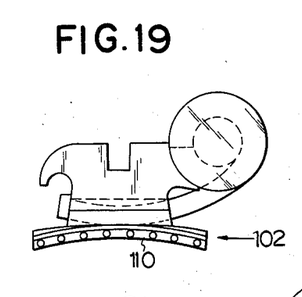
FIG. 19 is a side view of the orthodontic appliance shown in FIG. 18.

FIGS. 18 and 19 show a second embodiment of this invention which is similar to the first embodiment as above-described except for the shape of the mesh base 110 of bracket 102. The mesh base 110 is curved along a surface of a tooth to be moved.

Figure 20:
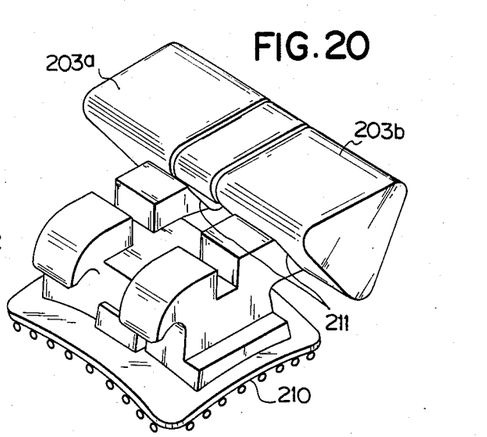
FIG. 20 is a perspective view showing an orthodontic appliance according to a third embodiment of this invention.
Figure 21:
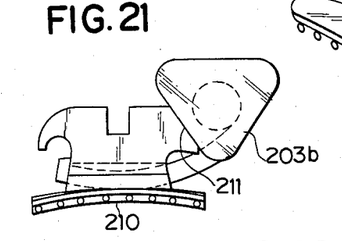
FIG. 21 is a side view of the orthodontic appliance shown in FIG. 20.

FIGS. 20 and 21 show a third embodiment of this invention which is similar to the second embodiment of FIGS. 18 and 19 except for the fact that magnet elements 203a, 203b are substantially triangular in section and that magnet bases 211 are flat. Any other cross-sectional shape for the magnet elements can be employed. Mesh base 210 is curved.

Figure 22:
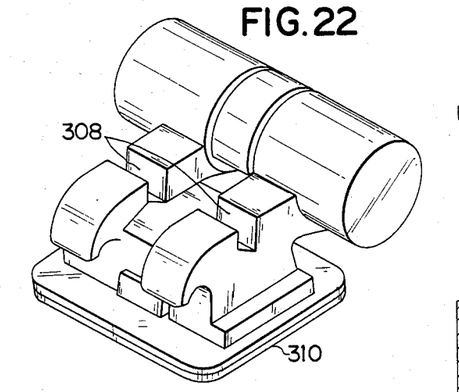
FIG. 22 is a perspective view showing an orthodontic appliance according to a fourth embodiment of this invention.
Figure 23:
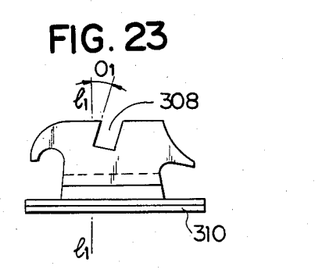
FIG. 23 is a side view of the orthodontic appliance shown in FIG. 22.

FIGS. 22 and 23 show a fourth embodiment of this invention which is similar to the first embodiment except for the configuration of groove 308 in the bracket. The groove 38 is inclined at an angle 01 with respect to the standard line 11—11 which is at a right angle to a flat mesh base 310. This is called a torqued bracket.

Figure 24:
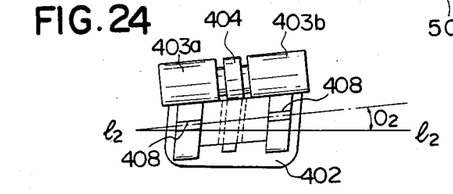
FIG. 24 is a front view showing an orthodontic appliance according to a fifth embodiment of this invention.
Figure 25:
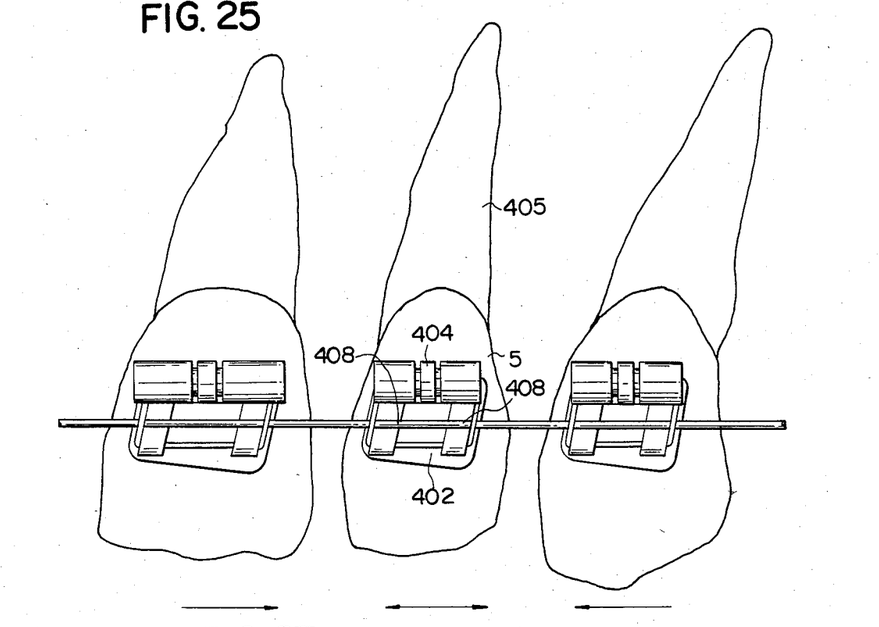
FIG. 25 shows a condition in which the orthodontic appliance of FIG. 24 is attached to teeth to be moved.

FIGS. 24 and 25 show a fifth embodiment of this invention. A slot or groove 408 is at an angulation angle 02 with respect to the standard line 12—12 of a bracket 402. The slot 408 is parallel to a pair of magnet elements 403a, 403b. The angulation angle is determined so as to the teeth 5 and the tooth roots 405 with a positive mesiodistal angulation.

Although not shown, both the torque angle 01 of FIGS. 22 and 23 and the angulation angle 02 of FIGS. 24 and 25 may be required to correct a certain condition.

FIGS. 26 to 29 show various types of holders for holding a magnet body 3.

Figure 26:
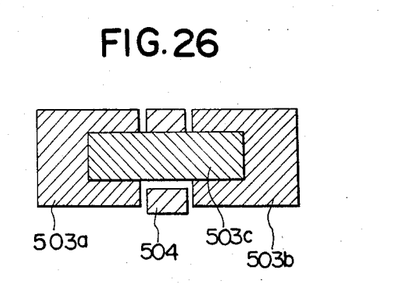
FIG. 26 is a sectional view showing a magnet attachment according to a sixth embodiment of this invention.

In the embodiment of FIG. 26, a pair of magnet elements 503a, 503b are joined through a pin 503c to a holder 504.

Figure 27:
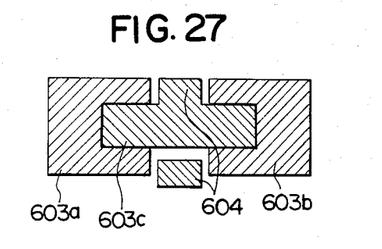
FIG. 27 is a sectional view showing a magnet attachment according to a seventh embodiment of this invention.

In the embodiment of FIG. 27, a pair of magnet elements 603a, 603b are joined to a pin portion 603c formed integrally with a holder 604.

Figure 28:
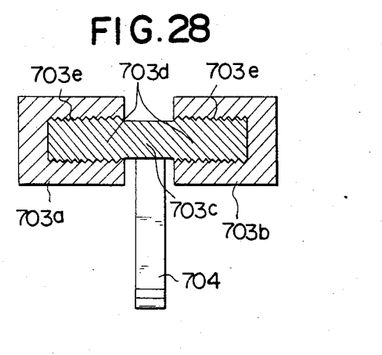
FIG. 28 is a sectional view showing a portion of a magnet attachment according to an eighth embodiment of this invention.
Figure 29:
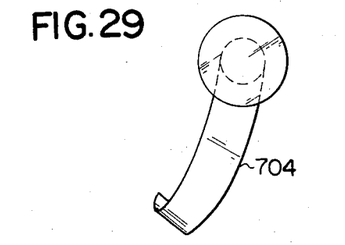
FIG. 29 is a side view showing the magnet attachment shown in FIG. 28.

In the embodiment of FIGS. 28 and 29, a pin 703c is integrally formed with a holder 704 in a T-shape and has a pair of male screw portions 703d which detachably engage a pair of female sockets 703e of magnet elements 703a, 703b.

Figures 39, 40, 41:
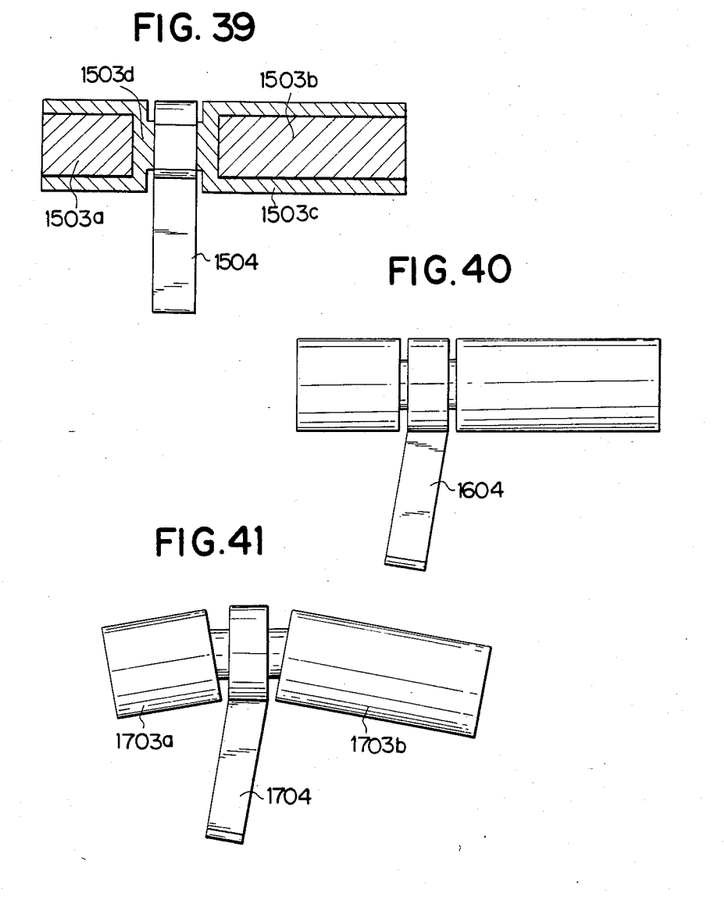
FIG. 39 is a sectional view showing a magnet attachment according to a seventeenth embodiment of this invention.
FIG. 40 is a plan view showing a magnet attachment according to an eighteenth embodiment of this invention.
FIG. 41 is a plan view showing a magnet attachment according to a nineteenth embodiment of this invention.

In the embodiment of FIG. 39, a magnet body includes a pair of magnet elements 1503a, 1503b each fixed in a cylindrical metal cover 1503c. In this case, a central slender joint portion 1503d of the metal cover 1503c may be formed integrally with a holder 1504.

Figure 30:
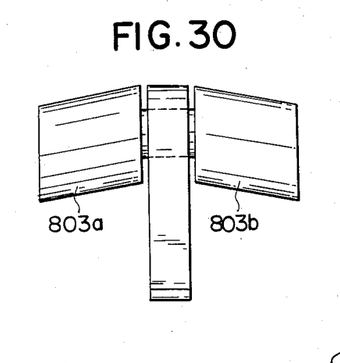
FIG. 30 is a perspective view showing an orthodontic appliance according to a ninth embodiment of this invention.
Figure 31:
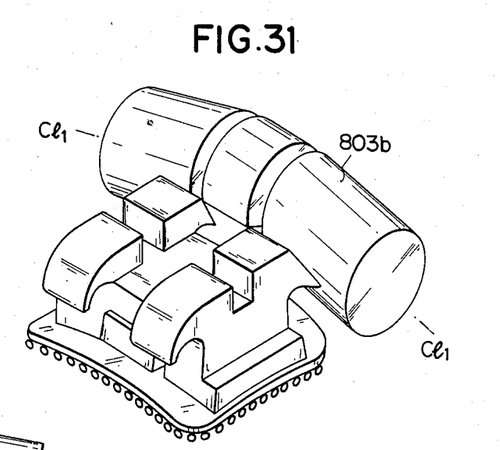
FIG. 31 is a front view of the orthodontic appliance shown in FIG. 30.

In the embodiment of FIGS. 30 and 31, magnet elements 803a, 803b are arranged along a curved line C11—C11 of the tooth surface 5a (FIG. 14) or a teeth arrangement (not shown).

Figure 32:
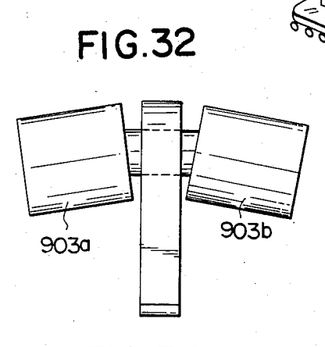
FIG. 32 is a plan view showing a magnet attachment according to a tenth embodiment of this invention.

In the embodiment of FIG. 32, magnet elements 903a, 903b are arranged in a curved line as in the embodiment of FIGS. 30 and 31 so that a magnetic traction force can be obtained in an ideal arch direction.

Figure 33:
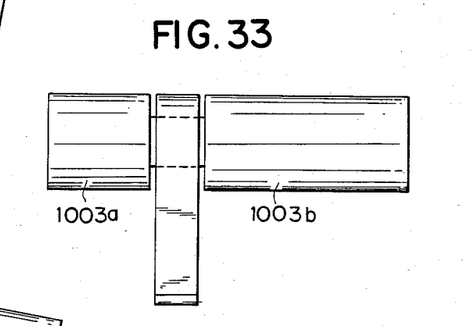
FIG. 33 is a plan view showing a magnet attachment according to an eleventh embodiment of this invention.

In the embodiment of FIG. 33, a holder is joined to a short magnet element 1003a and a long magnet element 1003b which are placed along a straight line.

Figure 34:
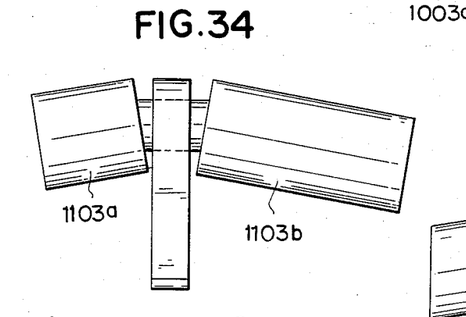
FIG. 34 is a plan view showing a magnet attachment according to a twelfth embodiment of this invention.
Figure 35:
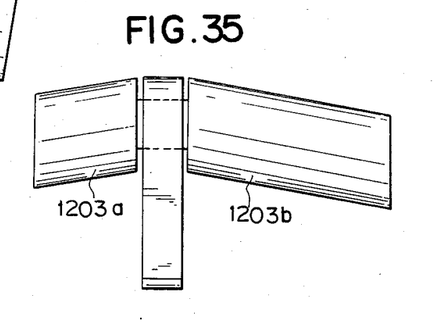
FIG. 35 is a plan view showing a magnet attachment according to a thirteenth embodiment of this invention.

In the embodiment of FIGS. 34 and 35, one magnet elements 1103a, 1203a are short while the other magnet elements 1103b, 1203b are long. Those magnet elements are placed along a curved line.

In the embodiments of FIGS. 1, 30 and 32-35, one magnet element can be replaced by a metal having no magnetic traction force such as a Ni-Cr alloy, a Co-Cr alloy, SUS and so on.

Figure 36:
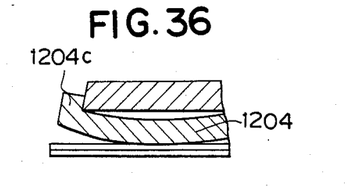
FIG. 36 is a sectional view showing a portion of a holder according to a fourteenth embodiment of this invention.
Figures 37, 38:
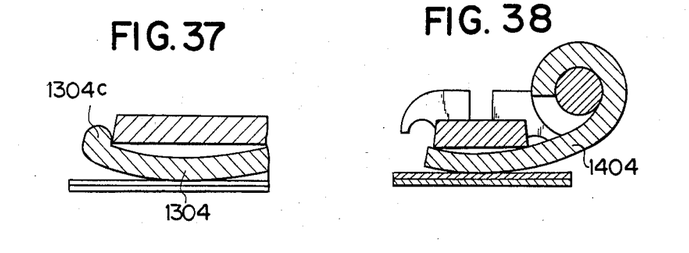
FIG. 37 is a sectional view showing a portion of a holder according to a fifteenth embodiment of this invention.
FIG. 38 is a sectional view showing a holder according to a sixteenth embodiment of this invention.

FIGS. 36 to 38 show various types of holders. In FIGS. 36 and 37, protruding stops 1204c, 1304c are formed at an end of a holders 1204, 1304 which stop at the securing opening 6 of the bracket 2 as in the first embodiment. In FIG. 38, no protruding stop is formed at a holder 1404.

In the embodiment of FIG. 40, a holder 1604 is bent in a mesial or distal direction.

In the embodiment of FIG. 41, a holder 1704 is bent in a mesial or distal direction and a pair of magnet elements 1703a, 1703b are arranged along a curved line.

All of the above-described embodiments can be used in substantially the same manner as the first embodiment of the FIGS. 1 to 13 so a detailed description and illustration thereof is omitted.

What is claimed is:

1. An orthodontic appliance for correcting teeth in a patient's mouth, said orthodontic appliance comprising:
   (a) a bracket adapted to be secured to one of the patient's teeth by means of an adhesive and having:
      i. a slot for receiving a correcting wire;
      ii. means for securing said bracket to said correcting wire; and
      iii. an aperture;
   (b) a magnet member; and
   (c) a holder for said magnet member in the form of a clip member secured to said magnet and having a curved, elastic elongated arm adapted to be received into said aperture of said bracket, said elongated arm resembling a leaf spring and carrying a protrusion for detachably latching onto said bracket.

2. The orthodontic appliance of claim 1 wherein said securing means is in the form of a plurality of wing portions on both sides of said slot and a ligature wire hooked onto said wing portions, over said correcting wire.

3. The orthodontic appliance of claim 1 wherein two of said wing portions are located on one side of said slot and each of said two wing portions has a shoulder contoured to the shape of said magnet for mating with said supporting said magnet.

4. The orthodontic appliance of claim 1 wherein said clip member is substantially the shape of the number "9".

5. An orthodontic appliance as defined in claim 1, wherein the bracket has a mesh base to be secured to the tooth of the patient by means of the adhesive.

6. An orthodontic appliance as defined in claim 5, wherein the mesh base is curved.

7. An orthodontic appliance as defined in claim 5, wherein the mesh base is flat.

8. An orthodontic appliance as defined in claim 1, wherein the magnet element is circular in cross-section.

9. An orthodontic appliance as defined in claim 1, wherein the magnet element is substantially triangular in cross-section.

10. An orthodontic appliance as defined in claim 1, wherein the bracket is a torqued bracket.

11. An orthodontic appliance as defined in claim 1, wherein the groove has an angulation angle.

12. An orthodontic appliance as defined in claim 1, further comprising a metal cover in which the magnet element is housed.

13. An orthodontic appliance as defined in claim 12, wherein the metal cover is formed integrally with the holder.

14. An orthodontic appliance as defined in claim 12, wherein the metal cover is separate from the holder.

15. An orthodontic appliance as defined in claim 1, wherein said magnet member comprises a joint portion and a pair of magnet elements fixed at both ends of said joint portion, the holder being secured to said joint portion.

16. An orthodontic appliance as defined in claim 15, wherein the holder is formed integrally with the joint portion of the magnet body.

17. An orthodontic appliance as defined in claim 15, wherein the holder is separate from the joint portion of the magnet body.

18. An orthodontic appliance as defined in claim 15, wherein the magnet elements have a common axis along a straight line.

19. An orthodontic appliance as defined in claim 15, wherein the magnet elements are arranged along a curved line.

20. An orthodontic appliance as defined in claim 15, wherein the magnet elements are of the same length.

21. An orthodontic appliance as defined in claim 15, wherein the magnet elements are different in length to each other.

22. An orthodontic appliance as defined in claim 15, wherein the magnet elements are different in magnetic force.

23. The orthodontic appliance of claim 1 wherein the bracket is provided with a seat portion which mates with and aligns said magnet body in a position parallel to said slot or groove.

24. The orthodontic appliance of claim 1 comprising the plurality of said brackets and magnet bodies mounting on said correcting wire with opposite poles of magnets on adjacent brackets in a facing relationship.

* * * * *